(12) United States Patent
Moon et al.

(10) Patent No.: US 8,039,631 B2
(45) Date of Patent: Oct. 18, 2011

(54) PROCESS FOR PREPARING CRYSTALLINE FORM A OF LANSOPRAZOLE

(75) Inventors: Seong Cheol Moon, Gyeonggi-do (KR); In Woong Song, Gyeonggi-do (KR); Doo Sung Kang, Gyeonggi-do (KR); Seong Soo Oh, Gyeonggi-do (KR); Sung Jae Lee, Seoul (KR)

(73) Assignees: Daewoong Pharmaceutical Co., Ltd., Sungnam-Si (KR); Daewoong Chemical Co., Ltd., Hwaseong-Si (KR)

( * ) Notice: Subject to any disclaimer, the term of this patent is extended or adjusted under 35 U.S.C. 154(b) by 569 days.

(21) Appl. No.: 12/159,922

(22) PCT Filed: Jan. 4, 2007

(86) PCT No.: PCT/KR2007/000048
§ 371 (c)(1),
(2), (4) Date: Sep. 16, 2008

(87) PCT Pub. No.: WO2007/078154
PCT Pub. Date: Jul. 12, 2007

(65) Prior Publication Data
US 2009/0018339 A1    Jan. 15, 2009

(30) Foreign Application Priority Data
Jan. 5, 2006  (KR) .................. 10-2006-0001303

(51) Int. Cl.
*C07D 401/12*    (2006.01)

(52) U.S. Cl. .................................................. 546/273.7
(58) Field of Classification Search ................ 546/273.7
See application file for complete search history.

(56) References Cited

U.S. PATENT DOCUMENTS

| 5,578,732 | A  | * | 11/1996 | Kato et al. | ................ | 546/273.7 |
| 6,002,011 | A  | * | 12/1999 | Kato et al. | ................ | 546/273.7 |
| 6,313,303 | B1 | * | 11/2001 | Tagami et al. | ............. | 546/273.4 |
| 2004/0010151 | A1 | | 1/2004 | Finkelstein et al. | | |

FOREIGN PATENT DOCUMENTS

| WO | WO-00/78745 A2 | 12/2000 |
| WO | WO-02/44167 A1 | 6/2002 |
| WO | WO-2004/018454 A1 | 3/2004 |

OTHER PUBLICATIONS

Kirk-Othmer Encyclopedia of Chemical Technology Copyright 2002 by John Wiley & Sons, Inc., pp. 95-147, Article Online Posting date: Aug. 16, 2002.*

* cited by examiner

*Primary Examiner* — Patricia Morris
(74) *Attorney, Agent, or Firm* — Birch, Stewart, Kolasch & Birch, LLP

(57) ABSTRACT

The present invention relates to a process for preparing Crystalline Form A of Lansoprazole. Specifically, the present invention relates to a process for preparing highly pure Crystalline Form A of Lansoprazole in a large scale without any additional conversion step, even by using ethanol in which Crystalline Form B is easily formed.

11 Claims, 1 Drawing Sheet

PROCESS FOR PREPARING CRYSTALLINE FORM A OF LANSOPRAZOLE

TECHNICAL FIELD

The present invention relates to a process for preparing Crystalline Form A of Lansoprazole. Specifically, the present invention relates to a process for preparing highly pure Crystalline Form A of Lansoprazole in a large scale without any additional conversion step, even by using ethanol in which Crystalline Form B is easily formed.

BACKGROUND ART

Lansoprazole of the following formula (1)

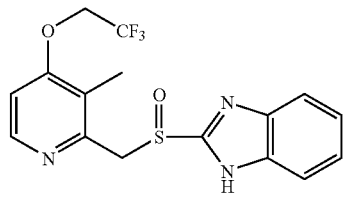

exhibits potent antibacterial activity, and is broadly used for treating gastric ulcer.

Lansoprazole is a proton pump inhibitor (PPI), and sweeps over the gastric ulcer market of the whole world, along with Omeprazole. *H. pylori*, one of the bacteria causing gastric ulcer, is completely controlled when Lansoprazole is administered together with Clarithromycin, and so Lansoprazole is very effective for the prevention of relapse as well as treatment of ulcer, and has excellent selectivity.

As the crystalline forms of Lansoprazole, Form A and Form B have been known [Farm vesin 1997, 48, 242-243, 290-291 (The Second Central European Symposium on Pharmaceutical Technology)]. As a matter of terminology, PCT/PL00/00042 (Instytut Farmacetutyczny) uses Form I and Form II, which are different from Form A and Form B, but have substantially same concepts as Form A and Form B. Further, US2004/0010151 (Nina Finkelstein, Shomit Wizel) [Lansoprazole Polymorphs and processes for preparation thereof] describes three forms of Lansoprazole: Form D, Form E, and Form F.

Crystalline Form A of Lansoprazole is used for the marketing agent, and is thermodynamically more stable than the Form B. That is, Form A has such high stability that it does not change even when stored for one year at room temperature or elevated temperature. On the other hand, Form B shows high stability when stored for one year at a low temperature (0° C. or lower), but shows some change in the crystalline form at elevated temperature. Thus, though Crystalline Form B of Lansoprazole has excellent solubility, Form A is used as medicine. In case of Forms D, F and F, the wet state (Form D) has a different form from the dry state (Form E). Conventionally, the crystalline form of Lansoprazole is obtained as a mixture of Forms A and D. Also, the crystalline form can be converted only through special processes that are industrially difficult to apply, such as applying mortar to convert the crystalline forms.

Many reports have been published for the preparing process of Crystalline Form B of Lansoprazole and for the conversion of Form B to Form A [PCT/PL00/00042; Farm vesin 1997, 48, 242-243, 290-291; and KR0433735 (C-Tri)]. The art-known processes for preparing Crystalline Form A of Lansoprazole may be summarized as follows:

[The First Process]

The method reported in Farm vesin shows that the conversion of Form B to Form A may occur according to the changes of temperature and mechanical stress. For example, the correlation between temperature and crystalline form conversion shows that Form B is slowly converted to Form A at a temperature of 10° C. or lower, but rapidly at 40° C. Further, the crystalline form conversion may be facilitated, as the mechanical stress on the Crystalline Form B of Lansoprazole changes. As the example, it is shown that the velocity of force during grinding or compression is correlated with the degree of crystalline form conversion.

However, in this method, the form of Lansoprazole present at the contact portion during grinding or compression may be converted, but that of Lansoprazole at the other portion does not change, and so pure Crystalline Form A of Lansoprazole is difficult to obtain. Therefore, to obtain pure Form A, the same process should be repeated, which requires a long operation time and also may cause polymorphism according to the conversion degrees of crystalline forms.

[The Second Process]

This method is reported in PCT/PL00/00042; and first prepares Form B and converts it to Form A. This method may be briefly summarized as follows.

Crude Lansoprazole prepared from the starting material 2-([3-methyl-4-(2,2,2-trifluoroethoxy)-2-pyridinyl]-methyl)thio-1H-benzimidazole is added to 90% ethanol, dissolved by heating to 55° C., filtered, and cooled to a low temperature (0° C. or lower). The resulting crystal is filtered to give Form B (Yield 90%). Thus prepared Crystalline Form B of Lansoprazole is added to acetone, refluxed, filtered, cooled to room temperature, slowly cooled to a lower temperature, and allowed to stand at 0° C. for 3 hours. The resulting crystal is filtered, and dried at a temperature of 50° C. or lower to give Form A (Yield 95%, Yield of the two steps 86%). However, this method has several problems that two steps of preparing Form B and converting Form B to Form A are required, thereby decreasing the total yield; the process should be repeated twice for conversion of the crystalline form; and the whole process requires a long time.

[The Third Process]

This method reported in KR 0433735 obtains Form A by vigorously stirring the Crystalline Form B of Lansoprazole in a solvent mixture of acetone and hexane for 1 hour, filtering the reaction mixture, and drying it for 2 hours. However, this method uses toxic hexane, and so is not appropriate to use industrially. Also, there is a risk that hexane may remain in the product.

The final step for preparing Lansoprazole is typically the oxidation of thio group (S) to sulfinyl group [S(=O)], during which ethanol is usually used as solvent [see EP 0 174 726 (Pyridine derivatives and their production)]. However, when ethanol is used as the crystallizing solvent, Form B is conventionally produced (see PCT/PL00/00042), and so it is expected that Lansoprazole prepared by using ethanol as solvent in the oxidation step is Form B. Thus, there has been a need to develop a process for preparing the Crystalline Form A of Lansoprazole directly from ethanol which is the solvent for preparing Lansoprazole by the oxidation of 2-([3-methyl-4-(2,2,2-trifluoroethoxy)-2-pyridinyl]-methyl)thio-1H-benzimidazole.

DISCLOSURE OF THE INVENTION

The present inventors extensively studied to develop a process for obtaining highly pure Crystalline Form A of Lansoprazole directly from ethanol used as solvent in the oxidation step, the last step for preparing Lansoprazole. As a result, the inventors have found that highly pure Crystalline Form A of Lansoprazole can be obtained by using water and ethanol as the crystallization solvent, and controlling the temperature and stirring time required for the crystallization to some ranges, to complete the present invention.

Therefore, the object of the present invention is to provide an effective process for preparing Crystalline Form A of Lansoprazole.

Hereinafter, the constitution of the present invention will be more specifically explained.

BEST MODE FOR CARRYING OUT THE INVENTION

Figure 1:
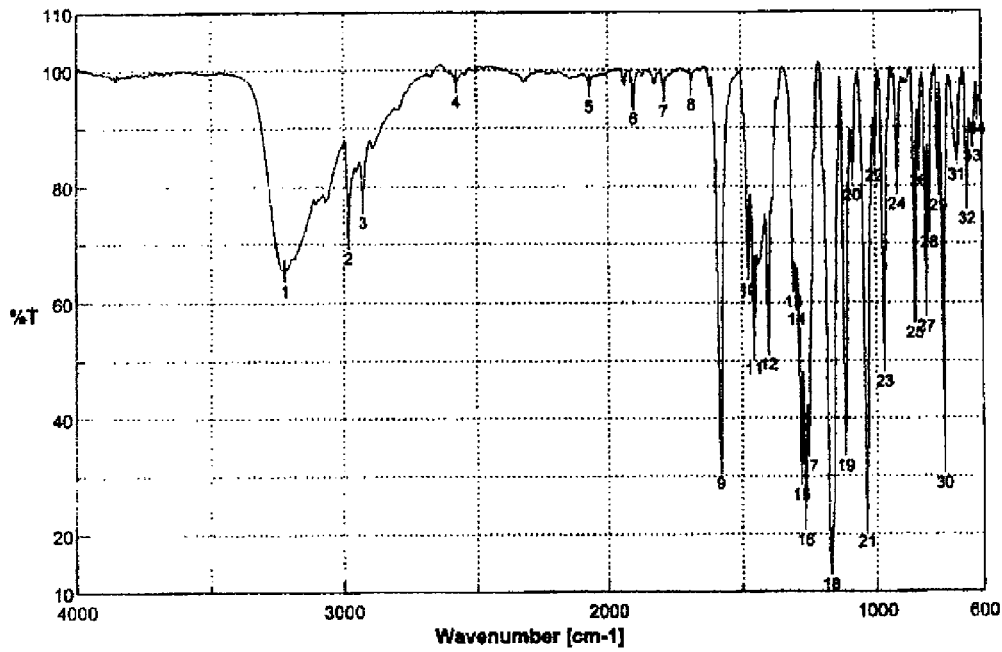
FIG. 1 represents the FT-IR spectrum of Crystalline Form A of Lansoprazole obtained in Example 1.

The present invention relates to a process for preparing the Crystalline Form A of Lansoprazole, which comprises dissolving Lansoprazole obtained by oxidation of 2-([3-methyl-4-(2,2,2-trifluoroethoxy)-2-pyridinyl]-methyl)thio-1H-benzimidazole in ethanol, adding water thereto, stirring the mixture at the temperature range of from 15 to 40° C. for 0.5 to 4 hours, and filtering and drying the resulting product.

Oxidation of the starting material 2-([3-methyl-4-(2,2,2-trifluoroethoxy)-2-pyridinyl]-methyl)thio-1H-benzimidazole may be carried out according to a conventional method known in an art (PCT/PL00/00042), for example, an oxidation method using such oxidants as m-chloroperbenzoic acid, magnesium monoperoxyphthalate, etc.

Crude Lansoprazole obtained from the oxidation is first dissolved in ethanol. Here, it is desirable to use ethanol of 95 to 99% purity in an amount of 1 to 50 parts by weight, preferably 20 to 30 parts by weight, per 1 part by weight of Lansoprazole. If necessary, the mixture may be heated to 40° C. in order for the crude Lansoprazole to be thoroughly solved.

When the crude Lansoprazole is dissolved in ethanol, the resulting solution may have some color due to the remaining impurities. Thus, charcoal and sodium hydrosulfite ($Na_2S_2O_4$) may be optionally added to the solution, which is then stirred for about 30 minutes, and filtered to remove the color. If the solution is acidified by adding charcoal, it is desirable to add such a base as potassium carbonate to adjust the pH of the solution to 8~9.

The crystallization of Lansoprazole is induced by adding water to the ethanol solution of the crude Lansoprazole. It is preferable to use water in an amount of 2 to 2.5 times by volume, particularly preferable 2 times by volume, to ethanol. Water is preferably added dropwise for 20 minutes to 1 hour, particularly preferably for 30 minutes. If water is poured at a time, the crystal is not formed properly, and so water should be added cautiously. After water is added, the solution is stirred for 0.5 to 4 hours, preferably 1 to 2 hours, under the condition that its temperature is maintained at 15 to 40° C., preferably 18 to 22° C. If the temperature is maintained at lower than 15° C. during the stirring, Form B is formed. If the temperature is maintained at higher than 40° C., the yield may decrease with forming Form B. Further, if the stirring time is less than 0.5 hour, Form B is formed, and if more than 4 hours, some quality problems such as color change, etc. in the product may happen. Thus, the exact control of temperature and stirring time is the key point to effectively obtain the Crystalline Form A of Lansoprazole according to the present invention.

The crystal obtained as above is filtered and dried according to conventional methods to give the desired Form A of Lansoprazole. Vacuum drying is usually applied to reduce time, and typically the crystal is dried for 4 to 24 hours, preferably 8 to 12 hours, at 35~40° C. Also, if necessary, the crystal may be dried under nitrogen pressure in a vacuum drier.

When the process of the present invention as explained above is used, the Form A of Lansoprazole is obtained in a high yield of about 95% and a high purity of 99 to 101%, to the authentic material.

Hereinafter, the present invention will be explained in more detail by the following Examples and Comparative Example. However, they are only presented to help the understanding on the present invention, but should not be construed as limiting the scope of the present invention in any way.

REFERENCE EXAMPLE 1

1.0 g (2.8 mmol) of 2-([3-methyl-4-(2,2,2-trifluoroethoxy)-2-pyridinyl]-methyl)thio-1H-benzimidazole was dissolved in 20 Ml of 95% ethanol, and cooled to −20~−10° C. 1.0 g (1.6 mmol) of 80% MMPP (magnesium monoperoxyphthalate) was added thereto, and the resulting mixture was stirred for 4 hours at the same temperature. Completion of the reaction was confirmed by TLC and HPLC, and 10 Ml of water was added to the reaction mixture, which was then stirred for 1 hour under ice-cooling. The reaction mixture was filtered to separate crystal, and thus separated crystal was washed with ice-cooled isopropanol-water mixture (1:1), and dried under reduced pressure, to give 0.98 g (Yield 95%) of Lansoprazole as white solid.

EXAMPLE 1

Figure 2:
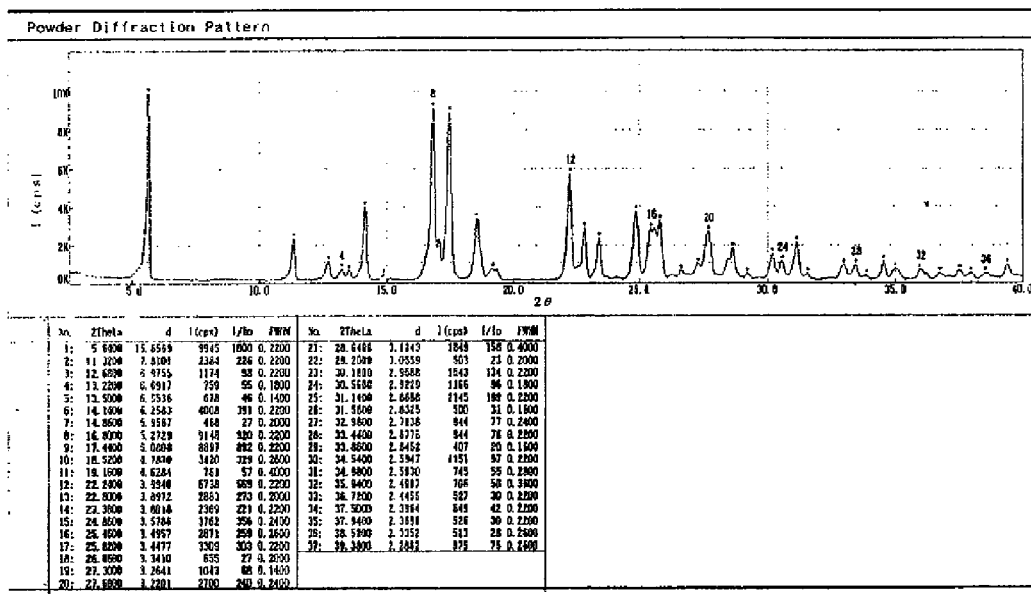
FIG. 2 represents the XRD spectrum of Crystalline Form A of Lansoprazole obtained in Example 1.

50 g of Lansoprazole prepared according to the Reference Example 1 was dissolved in 1 L of 95% ethanol at the temperature of 40° C. 5 g of charcoal and 90 mg of $Na_2S_2O_4$ were added thereto, and the pH of the resulting solution was adjusted to 8 by using $K_2CO_3$. The reaction mixture was stirred for 30 minutes, and filtered. 2 L of water was added dropwise to the filtrate over 30 minutes at 30° C. The reaction mixture was cooled to 20° C., and stirred for 2 hours. The crystal was filtered, dried under 40° C. vacuum for 8 hours, to give 46 g (Yield: 95%, Purity: 99.9%) of Lansoprazole Form A. Lansoprazole Form A thus obtained was identified by FT-IR (KBr; Jasco V530) and XRD (M18XHF-SRA) to show the same results as authentic Lansoprazole Form A (see FIGS. 1 & 2). Also, Lansoprazole Form A obtained by the present Example showed roughly three characteristic peaks in IR.

IR, $cm^{-1}$: 3234 (broad band), 2984, 2931, 1581, 1478, 1457, 1402, 1038, 972, 858

COMPARATIVE EXAMPLE 1

Process of PCT/PL00/00042

(Step 1)

35 g of Lansoprazole prepared according to the Reference Example 1 was added to 300 Ml of 90% ethanol, and heated to 55° C. in order to dissolve Lansoprazole. The resulting solution was filtered and cooled. The precipitate was filtered at 0° C. or lower, washed with 50 Ml of 50% ethanol, and dried at a temperature of not higher than 50° C., to give 31.5 g (Yield: 90%) of Form B of Lansoprazole containing a small amount of Form A.

(Step 2)

100 g of Lansoprazole obtained in Step 1 was added to 1500 Ml of boiling acetone, dissolved, and filtered. The filtrate was cooled to room temperature, slowly cooled to 0° C. over 3 hours, filtered again, and dried at a temperature of 50° C. or lower over 2 hours, to give 95 g (Yield: 95%) of Form A of Lansoprazole.

INDUSTRIAL APPLICABILITY

According to the process of the present invention, Crystalline Form A of Lansoprazole can be directly obtained from the solvent ethanol which is used in the oxidation process for preparing Lansoprazole.

The invention claimed is:

1. A process for preparing Crystalline Form A of Lansoprazole, which comprises dissolving Lansoprazole obtained by oxidation of 2-([3-methyl-4-(2,2,2-trifluoroethoxy)-2-pyridinyl]-methy)thio-1H-benzimidazole in ethanol, adding water, stirring the mixture at the temperature range of from 15 to 40° C. for 0.5 to 4 hours, filtering, and drying, said Crystalline Form A of Lansoprazole having the following X-ray powder diffraction peaks:

| No. | 2Theta | d | I (cps) | I/Io | FWHM |
|---|---|---|---|---|---|
| 1: | 5.6400 | 15.6569 | 9945 | 1000 | 0.2200 |
| 2: | 11.3200 | 7.8101 | 2384 | 226 | 0.2200 |
| 3: | 12.6800 | 6.9755 | 1174 | 98 | 0.2200 |
| 4: | 13.2200 | 6.6917 | 759 | 55 | 0.1800 |
| 5: | 13.5000 | 6.5536 | 678 | 46 | 0.1400 |
| 6: | 14.1400 | 6.2583 | 4008 | 391 | 0.2200 |
| 7: | 14.8600 | 5.9567 | 468 | 27 | 0.2000 |
| 8: | 16.8000 | 5.2729 | 9148 | 920 | 0.2200 |
| 9: | 17.4400 | 5.0808 | 97 | 892 | 0.2200 |
| 10: | 18.5200 | 4.7870 | 3420 | 329 | 0.2600 |
| 11: | 19.1600 | 4.6284 | 161 | 57 | 0.4000 |
| 12: | 22.2400 | 3.9940 | 5738 | 569 | 0.2200 |
| 13: | 22.8000 | 3.8972 | 2883 | 273 | 0.2000 |
| 14: | 23.3800 | 3.8018 | 2369 | 221 | 0.2200 |
| 15: | 24.8600 | 3.5786 | 3762 | 356 | 0.2400 |
| 16: | 25.4600 | 3.4957 | 2871 | 259 | 0.2600 |
| 17: | 25.8200 | 3.4477 | 3309 | 303 | 0.2200 |
| 18: | 26.6600 | 3.3410 | 655 | 270 | 0.2000 |
| 19: | 27.3000 | 3.2641 | 1043 | 68 | 0.1400 |
| 20: | 27.6800 | 3.2201 | 2700 | 240 | 0.2400 |
| 21: | 28.6400 | 3.1143 | 1849 | 158 | 0.4000 |
| 22: | 29.2900 | 3.0559 | 503 | 23 | 0.2000 |
| 23: | 30.1800 | 2.9588 | 1543 | 134 | 0.2200 |
| 24: | 30.5600 | 2.9229 | 1166 | 96 | 0.1800 |
| 25: | 31.1400 | 2.8698 | 2145 | 199 | 0.2200 |
| 26: | 31.5600 | 2.8325 | 500 | 31 | 0.1600 |
| 27: | 32.9800 | 2.7138 | 944 | 77 | 0.2400 |
| 28: | 33.4400 | 2.6775 | 944 | 76 | 0.2200 |
| 29: | 33.8600 | 2.6452 | 407 | 20 | 0.1600 |
| 30: | 34.5400 | 2.5947 | 1151 | 97 | 0.2200 |
| 31: | 34.9800 | 2.5630 | 745 | 55 | 0.2800 |
| 32: | 35.9400 | 2.4967 | 706 | 50 | 0.3600 |
| 33: | 36.7200 | 2.4455 | 527 | 30 | 0.2200 |
| 34: | 37.5000 | 2.3964 | 649 | 42 | 0.2200 |
| 35: | 37.9400 | 2.3696 | 526 | 30 | 0.2200 |
| 36: | 38.5200 | 2.3352 | 513 | 28 | 0.2600 |
| 37: | 39.3800 | 2.2862 | 975 | 75 | 0.2400. |

2. The process of claim 1, wherein ethanol is used in an amount of 1 to 50 parts by weight per 1 part by weight of Lansoprazole.

3. The process of claim 1 or 2, wherein the used ethanol has a purity of 95 to 99%.

4. The process of claim 1, wherein the color of the solution is removed by using charcoal and sodium hydrosulfite ($Na_2S_2O_4$) before water is added.

5. The process of claim 4, wherein the solution is adjusted to pH 8~9 by using a base.

6. The process of claim 1, wherein water is used in an amount of 2 to 2.5 times by volume to ethanol.

7. The process of claim 1, wherein water is added dropwise over from 20 minutes to 1 hour.

8. The process of claim 1, wherein the stirring temperature is controlled to 18 to 22° C. after water is added.

9. The process of claim 1, wherein the stirring time is controlled to 1 to 2 hours after water is added.

10. The process of claim 1, wherein the drying is carried out under vacuum.

11. The process of claim 10, wherein vacuum drying is carried out for 4 to 24 hours at 35~40° C.

\* \* \* \* \*